United States Patent
König et al.

(10) Patent No.: US 6,476,273 B2
(45) Date of Patent: *Nov. 5, 2002

(54) METHOD FOR PRODUCING PHOSPHONIUM PHENOLATES

(75) Inventors: Annett König, Krefeld (DE); Lothar Bunzel, Kempen (DE); Uwe Hucks, Alpen (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,475

(22) PCT Filed: Jun. 15, 1998

(86) PCT No.: PCT/EP98/03590

§ 371 (c)(1),
(2), (4) Date: Dec. 21, 1999

(87) PCT Pub. No.: WO99/00395

PCT Pub. Date: Jan. 7, 1999

(65) Prior Publication Data

US 2001/0005765 A1 Jun. 28, 2001

(30) Foreign Application Priority Data

Jun. 27, 1997 (DE) .......................... 197 27 351

(51) Int. Cl.$^7$ .................................................. C07F 9/54
(52) U.S. Cl. ............................................. 568/11; 568/9
(58) Field of Search ........................................ 568/9, 11

(56) References Cited

U.S. PATENT DOCUMENTS

| | | | | |
|---|---|---|---|---|
| 3,442,854 A | | 5/1969 | Curtius et al. ................. | 260/47 |
| 4,177,216 A | * | 12/1979 | Doorakian et al. | |
| 4,340,761 A | * | 7/1982 | Doorakian et al. ........... | 568/11 |
| 6,008,300 A | * | 12/1999 | Mizuide et al. ............. | 525/274 |

FOREIGN PATENT DOCUMENTS

EP 826693 * 3/1998

* cited by examiner

Primary Examiner—Jean F. Vollano
(74) Attorney, Agent, or Firm—Joseph C. Gil; Aron Preis

(57) ABSTRACT

A process for preparing phosphonium phenolate is disclosed. The process entails a reaction of phosphonium halide with phenol in an aqueous alkaline solution at a temperature of 0 to 55° C. The molar ratio of phenol to phosphonium halide is between 2:1 to 10:1 and the pH of the solution is 9.5 to 11. An optional embodiment entails carrying out the reaction in the further presence of alcohol.

5 Claims, No Drawings

METHOD FOR PRODUCING PHOSPHONIUM PHENOLATES

This is the national phase of PCT/EP98/03590, filed Jun. 15, 1998, now WO99/00395.

German application P 196 35 656.3 relates to a process for preparing phosphonium phenolates which is characterised in that phosphonium halides are reacted with phenols in a mixture of water, aqueous caustic alkali solution and inert solvent for between 2 minutes and 4 hours at temperatures from 0° C. to 40° C. and at pressures from 1 bar to 20 bar in the molar ratio 0.5 mol to 2 mol of phenol, preferably 0.7 to 1.3 moles of phenol, per mole of phosphonium halide.

$CH_2Cl_2$ and $C_6H_5Cl$ are mentioned as inert solvents in that document.

On page 4 of the German patent application P 196 35 656.3 it is also shown that phosphonium salts are converted into the corresponding phosphine oxide by bases. This is demonstrated in example A of this application, wherein a pH of about 14 is used. (See also comparison example in this application and German application P 19723524.7, which was filed on May 6, 1997 with intermediate priority date over P 19635656.3.)

During further development of this process it has now been found that alcohols which are sparingly soluble in water, that is up to a maximum of 15 wt. % solubility, may be used instead of inert solvents.

It was also found, surprisingly, that the formation of phosphine oxides is suppressed if the reaction is performed in alkaline solution, even without an alcohol, at a pH between 9.5 and 11, preferably between 9.5 and 10.5 and in particular between 10.0 and 10.5.

The present invention, therefore, provides a process for preparing phosphonium phenolates from phosphonium halides and phenols in aqueous alkaline solution at temperatures from 0 to 55° C., preferably 15 to 50° C., which is characterised in that the reaction is performed in the molar ratio of phenol to phosphonium halide between 2:1 and 10:1, preferably between 4.5:1 and 6:1 and in particular 5:1, at a pH of 9.5 to 11, preferably 9.5 to 10.5 and in particular 10 to 10.5 and optionally in the presence of alcohols in amounts of 50 wt. % to 200 wt. %, preferably 66 wt. % to 125 wt. %, with respect to the weight of the aqueous phase, wherein the alcohols have a solubility in pure water of at most 15 wt. %.

Phosphonium phenolates can be prepared in high yields using the process according to the invention.

Phosphonium phenolates are suitable in particular as catalysts for esterification and transesterification, in particular to prepare polycarbonates by the melt transesterification process (see U.S. Pat. No. 3,442,854).

The solubility of alcohols in water is known from the literature.

Suitable alcohols according to the invention are aliphatic alcohols with the formula $C_nH_{2n+1}OH$ in which n is an integer from 3 to 10 inclusive.

Suitable alcohols according to the invention are also cycloaliphatic alcohols with the formula $C_nH_{2n-1}OH$ in which n is an integer from 5 to 10 inclusive.

Preferred aliphatic alcohols are (iso)butanols, pentanols and hexanols, in particular isobutanol.

Preferred cycloaliphatic alcohols are cyclopentanol, cycloheptanol and cyclooctanol, in particular cyclohexanol.

The ratio by weight of water to alcohol is between 2:1 and 0.5:1, preferably between 1.5:1 and 0.8:1.

The sparingly soluble alcohols to be used according to the invention are added to facilitate the working-up procedure, since the phenol/alcohol mixture has a lower density than the aqueous solution and thus the organic phase is above the aqueous phase. The aqueous phase can thus be drawn off from below. The organic phase which contains the phenolate can then be washed with deionised water in the same separating vessel and the wash water can again be drawn off from below.

If an alcohol is not added, then the salt-containing aqueous solution is the only phase more dense than the organic phase and it can thus be drawn off from below. During the subsequent wash procedures using deionised water there is a phase inversion, the organic phase is then the denser phase and therefore is found below the aqueous phase. This working-up procedure has proven to be more costly in so far as a second processing vessel is required.

Phosphonium halides of the formula (I) are particularly suitable for the reaction according to the invention $$\left[R_1 - \overset{R_2}{\underset{R_3}{\overset{(+)}{P}}} - R_4\right]_n X_3^{(-)}, \quad (I)$$

$$\left[R_1 - \overset{R_2}{\underset{R_3}{\overset{(+)}{P}}} - R_4\right]_n X_n^{(-)}, \quad (I)$$

in which $R_1$ to $R_4$ are identical or different, and each represents a $C_1$–$C_{12}$ alkyl, $C_5$–$C_6$ cycloalkyl, $C_7$–$C_{12}$ aralkyl or $C_6$–$C_{14}$ aryl group,
and $X^{(-)}$ represents a halide ion, preferably $F^{(-)}$, $Cl^{(-)}$ or $Br^{(-)}$ and n is 1 or 2, wherein n is 2 when $R_4$ represents a $C_2$–$C_{12}$ alkylene group.

The groups $R_1$ to $R_4$ are identical or different, and each, preferably, represents a $C_6$–$C_{14}$ aryl group or the groups $R_1$ to $R_3$ each represent a $C_6$–$C_{14}$ aryl group and $R_4$ represents a $C_2$–$C_{12}$ alkylene group.

These types of phosphonium halides and methods for their preparation are known (see for example "Houben-Weyl, Methoden der organischen Chemie" volume XII/1, pages 79 et seq and Worrall, J. Amer. Chem. Soc, 52 (1930), pages 293 et seq).

These compounds (I) are produced during the reaction of trialkyl or triarylphosphines, for example triphenyl phosphine, with halogenated aromatic compounds or halogenated alkyl compounds, e.g. benzyl bromide, in the presence of metal salts (Friedel-Crafts alkylation) or in the presence of Grignard reagents and cobalt(II) chloride.

Preferred phenols are those of the formula (II)

$$\text{(II)}$$

in which $R_5$ to $R_7$, independently of each other, represent H, $C_1$–$C_{12}$ alkyl, $C_5$–$C_6$ cycloalkyl, $C_7$–$C_{12}$ arylalkyl and $C_6$–$C_{14}$ aryl groups; $R_5$ to $R_7$ are preferably hydrogen atoms.

These types of phenols are known from the literature.

Preferred phosphonium phenolates are thus those of the formula (III)

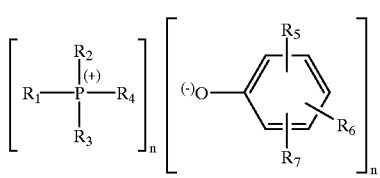

(III)

in which the groups $R_1$ to $R_7$ correspond to those in formulae (I) and (II) and n is again 1 or 2.

Deionised water or distilled water is preferably used for preparing the aqueous alkaline phase.

The pH can be adjusted to 9.5 to 11.0, preferably 9.5 to 10.5, in particular 10.0 to 10.5, using a caustic alkali solution, preferably caustic soda solution or caustic potash solution, taking into account the buffering effect of phenol/Na phenolate.

The process according to the invention may be performed continuously or batchwise, wherein a batchwise mode of operation is preferred.

According to a preferred mode of operation, phenol, phosphonium halide and alkanol as solution are initially introduced and water is then added. The pH is adjusted to 9.5 to 11.0, preferably 9.5 to 10.5, in particular 10.0 to 10.5 by adding caustic alkali solution, optionally with cooling. The temperature is maintained at 0 to 55° C., preferably 15 to 50° C., preferably with vigorous mixing of the reaction components. The reaction should be allowed to continue for a period of up to 2 hours, preferably up to 1 hour.

The phosphonium phenolate prepared according to the invention is preferably isolated, when using an alcohol which is sparingly soluble in water, by separating the aqueous phase from the organic phase, extracting the organic phase at least once, preferably 3 times, with deionised water or distilled water, then removing the alcohol, for example by distillation, and drying the reaction product after removing the phenol. If the phosphonium phenolate is produced in crystalline form during the two-phase boundary reaction according to the invention, these crystals may be recovered using conventional working-up procedures, inter alia by washing with deionised water or distilled water, optionally after recrystallising and drying.

If a sparingly soluble alcohol is not used, the precipitated crystals are extracted with deionised or distilled water.

Quaternary phosphonium phenols prepared according to the invention are in particular

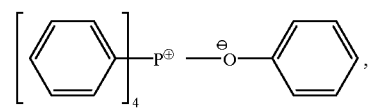

(IV)

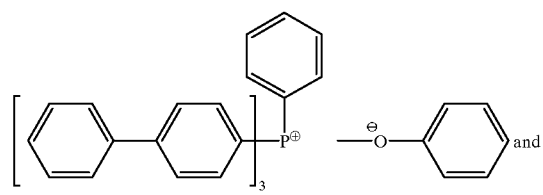

(V)

and

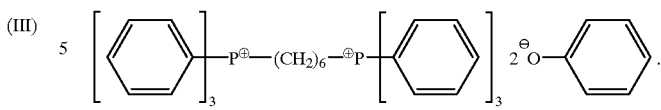

(VI)

Use of the phosphonium phenolates obtained according to the invention to prepare aromatic polycarbonates may take place in a manner known per se (see U.S. Pat. No. 3,442,854 loc cit).

As is well known the melt transesterification process uses, for example, aromatic diphenols, esters of diaryl carbonates and optionally branching agents and/or monophenols as starting materials.

The phosphonium phenolates obtained according to the invention are used in this process as catalysts in amounts of $10^{-1}$ moles to $10^{-8}$ moles, preferably in amounts of $10^{-3}$ moles to $10^{-7}$ moles, per mole of diphenol.

Further details relating to the melt transesterification process are described in the literature (see for example Hermann Schnell, Chemistry and Physics of Polycarbonates, Polymer Reviews, Vol 9, 1964, pages 44 to 51, DE-A 1 031 512, U.S. Pat. Nos. 3,022,272, 5,340,905 and 5,399,659).

Thermoplastic polycarbonates prepared using phosphonium phenolates obtained according to the invention are solvent-free, have an intrinsically pale colour and the final polycarbonate is largely free of unwanted defects.

The polycarbonates prepared in this way may be used on an industrial scale in the form of a very wide variety of moulded articles, in all areas in which thermoplastic polycarbonates have been used hitherto, for instance in electrical engineering components, as lamp covers, as safety shields or as CD material.

EXAMPLES

Comparison example (see example A in P 19635656.3 and P 19723524.7)

88.0 g (1.0 mol) of phenol, 88.0 g (0.99 mol) of 45% strength caustic soda solution and 1.5 l of triply deionised water are initially introduced into a 2.5 l round-bottomed flask with a stirrer, thermometer, reflux condenser and dropping funnel and stirred at 20° C. to 25° C. The pH is about 14. 41.93 g (0.10 mol) of tetraphenylphosphonium bromide are added to this solution. The mixture is then stirred for at least 0.5 hours. After phase separation, the organic phase is washed 3 times with triply deionised water and then evaporated down. The crystalline residue is dried at 100° C. under vacuum.

Example 1

470 g (5.0 mol) of phenol, 1.0 l of triply deionised water, 419.3 g (1 mol) of tetraphenylphosphonium bromide and 800 g of isobutanol are initially introduced into a 2.5 l round-bottomed flask with stirrer, thermometer and dropping funnel and stirred at 20° C. to 25° C. 106.7 g (1.2 mol) of 45% strength caustic soda solution are then added dropwise over the course of 2 minutes. The pH is checked using a glass electrode; it should be within the range 9.5 to 11.0. The mixture is then stirred for at least 0.5 hours at 45° C. After phase separation, the lower aqueous phase is drawn off and the organic phase is washed 3 times with triply deionised water. The wash water, as the denser phase, can be drawn from below each time. Then the isobutanol is distilled off at 50° C. under a water jet vacuum.

The crystalline residue is dried at 100° C. under vacuum. The yield determined by the P—NMR method is 98.2% of the theoretical yield.

Example 2

419.3 g (1 mol) of tetraphenylphosphonium bromide are dissolved in 940 g (10.0 mol) of phenol at 40 to 45° C. in a 5 l round-bottomed flask with stirrer, thermometer and dropping funnel, then 500 ml of triply deionised water are added. 133.3 g (1.5 mol) of 45% strength caustic soda solution are added dropwise over the course of 2 minutes. The pH is checked using a glass electrode; it should be within the range 9.5 to 11.0. The mixture is then stirred for at least 0.5 hours at 40 to 45° C. After phase separation, the aqueous phase (lower phase) is removed and the organic phase is washed 3 times with triply deionised water. A phase inversion occurs, since the aqueous phase is now less dense than the organic phase. The organic phase is drawn off and washed in a different vessel with triply deionised water, this process is repeated 3 times. A phenolic solution with 37% of tetraphenylphosphonium phenolate is obtained.

The yield determined by the P—NMR method is 100% of the theoretical yield.

Application examples

B1) 114.15 g (0.500 mol) of bisphenol A and 113.54 g (0.530 mol) of diphenyl carbonate are weighed into a 500 ml 3-necked flask with stirrer, internal thermometer and Vigreux column (30 cm, with plates) with bridges. Atmospheric oxygen is removed from the apparatus by applying a vacuum and flushing with nitrogen (3 times) and the mixture is heated to 150° C. Then 0.0173 g ($4 \times 10^{-3}$ mol. %) of tetraphenylphosphonium phenolate (TPP—P) prepared in accordance with example 1, with respect to the bisphenol A, is added as a 3% strength phenolic solution and the phenol produced is distilled off at 100 mbar. At the same time the temperature is increased to 250° C. The pressure is then decreased stepwise down to 1 mbar and the temperature is increased to 260° C. Then the temperature is increased to 280° C. and the mixture is stirred for 1.5 hours at 0.1 mbar. A pale coloured, solvent-free polycarbonate with a relative solution viscosity of 1.250 (dichloromethane, 25° C., 5 g/l) is obtained.

The concentration of branching agent of the formula (VII) in the polycarbonate prepared is 25 ppm. The phenolic OH-value of the polycarbonate is 70 ppm.

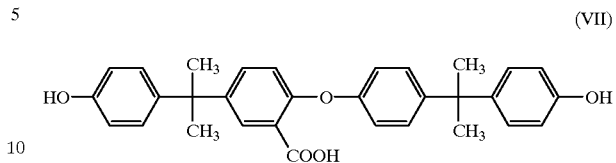

(VII)

B2) As in example B1), except that the temperature is increased from 260° C. to 300° C. and the mixture is stirred for 1.5 hours at 0.1 mbar. A pale coloured, solvent-free polycarbonate with a relative solution viscosity of 1.300 (dichloromethane, 25° C., 5 g/l) is obtained. The concentration of branching agent of the formula (VII) in the polycarbonate prepared is 18 ppm. The phenolic OH-value of the polycarbonate is 55 ppm.

What is claimed is:

1. A process for preparing phosphonium phenolate comprising a reaction of phosphonium halide with phenol in a medium consisting of aqueous alkaline solution at a temperature of 0 to 55° C., wherein molar ratio of phenol to phosphonium halide is between 2:1 to 10:1 and wherein pH is 9.5 to 11.

2. The process of claim 1 wherein said medium further contains alcohol in an amount of 50 to 200 percent relative to the weight of the aqueous phase of said solution, said alcohol having solubility in water of at most 15 percent by weight.

3. The process of claim 1 wherein pH of said aqueous alkaline solution is 9.5 to 10.5.

4. The process of claim 1 wherein pH of said aqueous alkaline solution is 10 to 10.5.

5. The process of claim 2 wherein amount of alcohol is 66 to 125 wt %.

* * * * *